United States Patent [19]

Chan

[11] 4,061,773

[45] Dec. 6, 1977

[54] GLYCYRRHETINIC ACID DERIVATIVES

[75] Inventor: Rosalind Po Kuen Chan, London, England

[73] Assignee: Biorex Laboratories Limited, London, England

[21] Appl. No.: 651,594

[22] Filed: Jan. 22, 1976

[30] Foreign Application Priority Data

Feb. 7, 1975 United Kingdom .................. 5296/75

[51] Int. Cl.$^2$ ...................... A61K 31/22; C07C 69/34; C07C 69/74

[52] U.S. Cl. ......................................... 424/313; 560/6; 560/194

[58] Field of Search ........................ 260/485 L, 468.5; 424/313

[56] References Cited

U.S. PATENT DOCUMENTS 3,452,078  6/1969  Turner et al. ..................... 260/468.5

FOREIGN PATENT DOCUMENTS 1,227,547  4/1971  United Kingdom .............. 260/468.5

*Primary Examiner*—Jane S. Myers
*Attorney, Agent, or Firm*—Wenderoth, Lind & Ponack

[57] ABSTRACT

The present invention provides new glycyrrhetinic acid derivatives of the general formula:

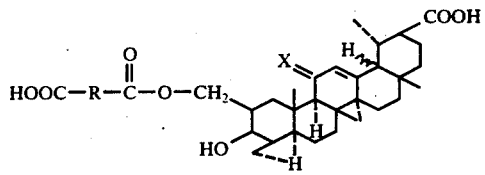

wherein R is an alkylene or cycloalkylene radical and X represents an oxygen atom or two hydrogen atoms; and the non-toxic salts and esters thereof.

18 Claims, No Drawings

GLYCYRRHETINIC ACID DERIVATIVES

BACKGROUND OF THE INVENTION

Numerous compounds are already known for the treatment of inflammatory conditions in mammals, including humans, and it is an object of the present invention to provide a new group of valuable and effective anti-inflammatory agents.

Several derivatives of glycyrrhetinic acid are already known which have a good anti-inflammatory action but which suffer from the disadvantageous side effect of being anti-diuretic. It is, therefore, a further object of the present invention to provide new and anti-inflammatory derivatives of glycyrrhetinic acid which do not have a serious anti-diuretic side effect.

SUMMARY OF THE INVENTION

The present invention provides new glycyrrhetinic acid derivatives of the general formula:

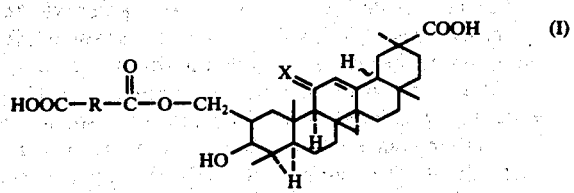

wherein R is an alkylene or cycloalkylene radical and X represents an oxygen atom or two hydrogen atoms; and the non-toxic salts and esters thereof.

DETAILED DESCRIPTION OF THE INVENTION

The alkylene or cycloalkylene radical R preferably contains up to 10 carbon atoms and more preferably contains up to 6 carbon atoms. When R is an alkylene radical, it is preferably of the type $-(CH_2)_n-$, in which $n$ is a whole number of from 1 to 10 and preferably of from 1 to 6, and when R is a cycloalkylene radical, it is preferably a cyclohexyl radical.

The new compounds according to the present invention have an excellent anti-inflammatory activity and, in contradistinction to many known glycyrrhetinic acid derivatives, do not have a significant anti-diuretic activity.

The new compounds according to the present invention can be prepared, for example, by reacting 2-hydroxymethyl-18α- or -18β-glycyrrhetinic acid or 2-hydroxymethyl-11-deoxo-18α- or -18β-glycyrrhetinic acid with a reactive derivative of an appropriate aliphatic or cycloaliphatic dicarboxylic acid, for example an anhydride thereof. Instead of the free acids, it is also possible to use the corresponding esters as starting material. In this way, compounds (I) are obtained in which the 30-oic acid group is esterified.

The compounds (I) thus obtained can then be converted into non-toxic salts, for example, by reaction with a basic metal or ammonium compound, such as ammonium, sodium, potassium, calcium or magnesium hydroxide or carbonate. Other metal salts can be prepared by reacting a water-soluble salt of a compound (I) with an appropriate water-soluble metal salt, for example, by the reaction of a sodium salt of a compound (I) with copper, magnesium or iron sulphate.

If desired, the compounds (I) can be esterified to give the corresponding diesters, for example, by reaction with an appropriate diazo compound, such as diazomethane. When an ester has been used as starting material, then subsequent esterification of the product can be used to give a compound in which the two ester groupings are the same or different.

The 2-hydroxymethyl-18α- and -18β-glycyrrhetinic acid used as starting material can be prepared, for example, from ethyl 2-hydroxymethylene-3-keto-glycyrrhetinate by reduction to ethyl 2-hydroxymethyl-glycyrrhetinate, followed by saponification thereof.

The 2-hydroxymethyl-11-deoxo-18α- and -18β-glycyrrhetinic acid also used as starting material can be prepared in an analogous manner, for example, from ethyl 2-hydroxymethylene-3-keto-11-deoxo-glycyrrhetinate.

The following Examples are given for the purpose of illustrating the present invention:

EXAMPLE 1 a. A suspension of 32 g. ethyl 2-hydroxymethylene-3-keto-18α-glycyrrhetinate (m.p. 242° – 244° C.) in 700 ml. ethanol was mixed with a solution of 5 g. sodium borohydride in 100 ml. ethanol at 0° – 20° C. and stirred for 6 hours. The reaction mixture was then poured into a mixture of ice and 2N hydrochloric acid and the precipitate formed was filtered off and dissolved in chloroform. The chloroform solution was washed with water, dried over anhydrous sodium sulphate and evaporated to dryness. The residual gum was taken up with 100 ml. benzene and filtered through a column containing 300 g. neutral alumina packed in benzene. The column was eluted with 1 liter of a mixture of chloroform and benzene (1:3 v/v) and the eluant discarded. Further elution with 1 liter of a mixture of chloroform and benzene (1:1 v/v) and with 1 liter of a mixture of chloroform and benzene (1:1 v/v) containing 5% methanol gave 25 g. of product which, after recrystallisation from diethyl ether, gave ethyl 2-hydroxymethyl-18α-glycyrrhetate; m.p. 228° – 231° C.; $[\alpha]_D = +111°$ (c. = 1% in chloroform).

b. 12 g. ethyl 2-hydroxymethyl-18α-glycyrrhetate in 150 ml. 5% methanolic potassium hydroxide were heated under reflux for 5 hours. After cooling, the reaction mixture was acidified with 2N hydrochloric acid and the precipitate obtained was filtered off, washed with water and sucked dry. The product obtained was recrystallised twice from a mixture of dichloromethane and methanol (3:1 v/v) to give needles of 2-hydroxymethyl-18α-glycyrrhetinic acid; m.p. 288° – 291° C. (dec.); $[\alpha]_D = +93°$ (c. = 0.5% in methanol).

c. A solution of 11 g. 2-hydroxymethyl-18α-glycyrrhetinic acid in 150 ml. pyridine was treated with 12 g. purified glutaric anhydride at 20° C. for 3 days, whereafter thin layer chromatography showed the reaction to be complete. The reaction mixture was poured into a mixture of ice and 2N hydrochloric acid and stirred for 30 minutes. The precipitate was filtered off, taken up in chloroform, washed with water, dried over anhydrous sodium sulphate and evaporated to dryness. The residue was decolorised by dissolving it in 100 ml. chloroform, filtering the solution through a thick pad of silica gel (BDH, 60 – 120 mesh) and washing the pad with a further 300 ml. chloroform. Evaporation of the chloroform solution gave 2-carboxybutyroxymethyl-18α-glycyrrhetinic acid in the form of a gum, which could not be crystallised. Thin layer chromatography (5% methanol in chloroform; Rf = 0.49) showed that the compound was pure.

d. 10.6 g. 2-carboxybutyroxymethyl-18α-glycyrrhetinic acid in 100 ml. methanol were treated with a solution of 1.38 g. sodium hydroxide in 20 ml. 90% aqueous methanol. The resulting solution was concentrated at a low temperature and acetone was added to the concentrate, whereafter it was left to crystallise at 0° C. The crystals obtained were recrystallised from the same solvent mixture to give the disodium salt of 2-carboxybutyroxymethyl-18α-glycyrrhetinic acid; m.p. 330° C.; $[\alpha]_D = +77°$ (c. = 1% in methanol).

e. 2-Carboxybutyroxymethyl-18α-glycyrrhetinic acid was reacted in ether with diazomethane to give the corresponding dimethyl ester in the form of a gum, the structure of which was confirmed by its NMR spectrum.

EXAMPLE 2 a. A solution of 3 g. ethyl 2-hydroxymethyl-18α-glycyrrhetate in 50 ml. glacial acetic acid was treated with a trace of perchloric acid and 150 mg. Adams' catalyst. The mixture was shaken in hydrogen for 7 hours and then filtered. The filtrate was diluted with water and the precipitate formed was filtered off, thoroughly washed with water and dried. The material thus obtained was heated under reflux for 3 hours in 100 ml. of a 5% methanolic solution of sodium hydroxide. After cooling, the mixture was poured into dilute hydrochloric acid and ice, followed by extraction with dichloromethane. Evaporation of the extract gave 2.3 g. 2-hydroxymethyl-3β-hydroxy-18α-olean-12-en-30-oic acid which melted, with sintering, at 202° - 204° C.; $[\alpha]_D = +75°$ (c. = 1% in methanol).

b. 11.5 g. 2-Hydroxymethyl-3β-hydroxy-18α-olean-12-en-30-oic acid in 70 ml. dry piperidine were mixed with 12 g. glutaric anhydride and the reaction mixture was stirred for 4 days at 20° C. The reaction mixture was then poured into dilute hydrochloric acid and ice and stirred for 1 hour. The precipitate formed was filtered off, washed with water and dried. The dry material was dissolved in diethyl ether and treated with charcoal. After filtering off the charcoal, the filtrate was evaporated to give 12 g. 2-carboxybutyroxymethyl-3β-hydroxy-18α-olean-12-en-30-oic acid in the form of a gum.

c. A solution of 10.5 g. 2-carboxybutyroxymethyl-3β-hydroxy-18α-olean-12-en-30 -oic acid in 100 ml. methanol was treated dropwise, while stirring and cooling, with 20 ml. of aqueous methanol containing 1.4 g. sodium hydroxide. The pH of the solution obtained was adjusted to 8 and then concentrated by evaporation under reduced pressure. Acetone was added, with cooling, to the concentrated solution and the product which separated out was filtered off. There were obtained 11 g. of the disodium salt of 2-carboxybutyroxymethyl-3β-hydroxy-18α-olean-12-en-30-oic acid; m.p. > 340° C.; $[\alpha]_D = +70°$ (c. = 1% in methanol).

EXAMPLE 3 a. A solution of 10 g. ethyl 2-hydroxymethyl-18α-glycyrrhetate (see Example 1(a)) and 12 g. glutaric anhydride in 70 ml. pyridine was left at ambient temperature for 3 days and then poured into dilute hydrochloric acid. The mixture was stirred for 30 minutes and the precipitate obtained was filtered off and washed with water. It was then dissolved in diethyl ether, dried over anhydrous sodium sulphate and treated with charcoal. After filtration and evaporation of the filtrate, there was obtained ethyl 2-carboxybutyroxymethyl-18α-glycyrrhetate in the form of a gum. Thin layer chromatography showed the gum to be more than 99% pure.

b. 11.5 g. ethyl 2-carboxybutyroxymethyl-18α-glycyrrhetate in 100 ml. ethanol was stirred with a 1% aqueous ethanolic solution of sodium hydroxide until the pH of the solution was 7.8. The solvent was removed and the residual gum was boiled with diethyl ether and decanted to give 10.5 g. of the sodium salt of ethyl 2-carboxybutyroxymethyl-18α-glycyrrhetate in the form of an amorphous solid; $[\alpha]_D = +81°$ (c. = 1% in methanol).

EXAMPLE 4 a. A solution of 32 g. pimelic acid in 300 g. dry diethyl ether was added portionwise, while stirring, to 40 g. dicyclohexyl carbodiimide in 100 ml. dry diethyl ether. The mixture was stirred for 24 hours and filtered. The filtrate was evaporated to give pimelic anhydride in the form of a thick oil. This was taken up in 150 ml. dry pyridine and treated with 12 g. 2-hydroxymethyl-18α-glycyrrhetinic acid. The solution was stirred and left for 5 days, whereafter it was poured into dilute hydrochloric acid and ice. After stirring the mixture for 1 hour, the gummy precipitate was separated off, dissolved in diethyl ether, washed with dilute hydrochloric acid and water, dried over anhydrous sodium sulphate and treated with charcoal. After filtration and evaporation of the filtrate, there was obtained 2-carboxyhexanoyloxymethyl-18α-glycyrrhetinic acid in the form of a gum.

b. The 2-carboxyhexanoyloxymethyl-18α-glycyrrhetinic acid gum obtained above in (a) was treated in 100 ml. methanol with a 1% aqueous methanolic solution of sodium hydroxide until the pH had reached 7.8. The solution was concentrated to a small volume and acetone added to the concentrate, a gummy solid precipitate being obtained. This was separated and crystallised from methanol and acetone (1:3) to give 8.5 g. of the disodium salt of 2-carboxyhexanoyloxymethyl-18α-glycyrrhetinic acid; m.p. > 280° C. (decomp.); $[\alpha]_D = +75°$ (c. = 1% in methanol).

EXAMPLE 5 a. A solution of 12 g. 2-hydroxymethyl-18α-glycyrrhetinic acid and of 15 g. cis-cyclohexane-1,2-dicarboxylic anhydride in 150 ml. dry pyridine was left to stand at ambient temperature for 4 days, whereafter it was poured into dilute hydrochloric acid and ice. The mixture was stirred for 1 hour and filtered. The material thus obtained was taken up in chloroform, washed with water, dried over anhydrous sodium sulphate and the chloroform evaporated to give a gum which crystallised upon the addition of ether. Recrystallisation from methanol and diethyl ether (1:9) gave 12.8 g. of pure 2-(2-carboxycyclohexylcarboxy)-methyl-18α-glycyrrhetinic acid; m.p. 247° - 249° C.; $[\alpha]_D = +84°$ (c. = 1% in methanol).

b. A solution of 11 g. 2-(2-carboxycyclohexylcarboxy)-methyl-18α-glycyrrhetinic acid in 120 ml. methanol was treated with a 5% aqueous methanolic solution of sodium hydroxide until the pH reached 7.8. The solution was evaporated to dryness under reduced pressure. The residual gum obtained was crystallised from methanol-acetone (1:4) to give 11 g. of the disodium salt of 2-(2-carboxycyclohexylcarboxy)-methyl-18α-glycyrrhetinic acid; m.p. > 300° C.; $[\alpha]_D = +77°$ (c. = 1% in methanol).

EXAMPLE 6 a. A solution of 10.5 g. 2-hydroxymethyl-18α-glycyrrhetinic acid and 12 g. succinic anhydride in 120 ml. dry pyridine was left at ambient temperature for 40 hours and then poured into dilute hydrochloric acid and ice. The mixture was then stirred for 1 hour and filtered. The material obtained was taken up in 150 ml. chloroform, washed with water and dried over anhydrous sodium sulphate. After filtering and evaporation of the filtrate, a gum was obtained which was crystallised from diethyl ether-dichloromethane (3:1) to give 11 g. of 2-carboxypropionyloxymethyl-18α-glycyrrhetinic acid; m.p. 203° – 204° C.; $[\alpha]_D = + 104°$ (c. = 1% in chloroform).

b. A solution of 10.5 g. 2-carboxypropionyloxymethyl-18α-glycyrrhetinic acid in 100 ml. methanol was treated with a 5% aqueous methanolic solution of sodium hydroxide until the pH of the solution was 7.6 – 7.8. The solution was evaporated to dryness under reduced pressure and the residue was crystallised from methanol-acetone (1:3) to give 10.2 g. of the disodium salt of 2-carboxypropionyloxymethyl-18α-glycyrrhetinic acid; m.p. > 300° C. (decomp.); $[\alpha]_D = + 84°$ (c. = 0.5% in methanol).

The present invention also includes within its scope pharmaceutical compositions containing at least one of the new compounds of general formula (I), in admixture with a solid or liquid pharmaceutical carrier.

Solid compositions for oral administration include compressed tablets, pills, dispersible powders and granules. In such solid compositions, one of the new compounds is admixed with at least one inert diluent, such as calcium carbonate, starch, alginic acid or lactose. The compositions may also comprise, as is normal practice, additional substances other than inert diluents, for example, lubricating agents, such as magnesium stearate.

Liquid compositions for oral administration include pharmaceutically acceptable emulsions, solutions, suspensions, syrups and elixirs containing inert diluents commonly used in the art, such as water and liquid paraffin. Besides inert diluents, such compositions may also comprise adjuvants, such as wetting and suspension agents, and sweetening and flavoring agents.

The compositions according to the present invention, for oral administration, include capsules of absorbable material, such as gelatine, containing one of the new derivatives, with or without the addition of diluents or excipients.

Preparations according to the present invention for parenteral administration include sterile aqueous or non-aqueous solutions, suspensions or emulsions. Examples of non-aqueous solvents or suspending media include propylene glycol, polyethylene glycol, vegetable oils, such as olive oil, and injectable organic esters, such as ethyl oleate. These compositions may also contain adjuvants, such as wetting, emulsifying and dispersing agents. They may be sterilised, for example, by filtration through bacteria-retaining filters, by incorporation into the compositions of sterilising agents, by irradiation or by heating. They may also be produced in the form of sterile solid compositions, which can be dissolved in sterile water or some other sterile injectable medium immediately before use.

The compositions according to the present invention for topical application include lotions, creams, pastes, ointments and liniments.

The percentage of active material in the compositions of the present invention may be varied, it being necessary that it should constitute a proportion such that a suitable dosage for the desired therapeutic effect shall be obtained. In general, the preparations of the present invention should be administered orally or parenterally to humans to give 10 to 1000 mg. and preferably 50 – 500 mg. of active substance per day.

The following Examples illustrate pharmaceutical compositions according to the present invention:

EXAMPLE 7

250 mg. tablets are prepared containing:

| | | |
|---|---|---|
| disodium salt of 2-carboxybutyroxymethyl-18α-glycyrrhetinic acid | 50 | mg. |
| starch | 100 | mg. |
| lactose | 95 | mg. |
| magnesium stearate | 5 | mg. |

EXAMPLE 8

400 mg. tablets are prepared containing:

| | | |
|---|---|---|
| 2-carboxybutyroxymethyl-18α-glycyrrhetinic acid | 25 | mg. |
| starch | 150 | mg. |
| lactose | 215 | mg. |
| magnesium stearate | 10 | mg. |

The compositions according to Examples 7 and 8 are intended for oral administration to humans for the treatment of inflammatory conditions.

I claim:

1. A compound of the formula

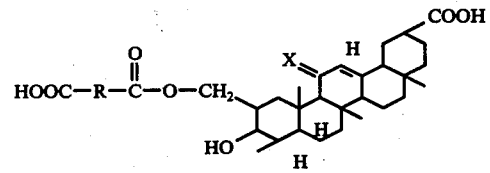

wherein R is alkylene of 1–10 carbon atoms and X represents an oxygen atom or two hydrogen atoms; or a non-toxic salt or methyl or ethyl ester thereof.

2. A compound according to claim 1, wherein R is alkylene of 1–6 carbon atoms.

3. A compound according to claim 2, which is 2-carboxybutyroxymethyl-18α-glycyrrhetinic acid.

4. A compound according to claim 2, which is 2-carboxybutyroxymethyl-3β-hydroxy-18α-olean-12-en-30-oic acid.

5. A compound according to claim 2, which is ethyl 2-carboxybutyroxymethyl-18α-glycyrrhetinic acid.

6. A compound according to claim 2, which is 2-carboxyhexanoyloxymethyl-18α-glycyrrhetinic acid.

7. A compound according to claim 2, which is 2-carboxypropionyloxymethyl-18α-glycyrrhetinic acid.

8. A compound according to claim 2, which is the disodium salt of 2-carboxybutyroxymethyl-18α-glycyrrhetinic acid.

9. A compound according to claim 2, which is the dimethyl ester of 2-carboxybutyroxymethyl-18α-glycyrrhetinic acid.

10. A compound according to claim 2, which is the disodium salt of 2-carboxybutyroxymethyl-3β-hydroxy-18α-olean-12-en-30-oic acid.

11. A compound according to claim 2, which is the sodium salt of ethyl 2-carboxybutyroxymethyl-18α-glycyrrhetinic acid.

12. A compound according to claim 2, which is the disodium salt of 2-carboxyhexanoyloxymethyl-18α-glycyrrhetinic acid.

13. A compound according to claim 2, which is the disodium salt of 2-carboxypropionyloxymethyl-18α-glycyrrhetinic acid.

14. A pharmaceutical composition comprising a compound according to claim 1 in admixture with a solid or liquid pharmaceutical diluent or carrier.

15. A composition according to claim 14, wherein R is alkylene of 1-6 carbon atoms.

16. A method of treating inflammatory conditions in mammals, which comprises administering topically, orally, rectally or parenterally a therapeutically effective amount of a compound according to claim 1 to the mammal.

17. A method according to claim 16, wherein R is alkylene of 1-6 carbon atoms.

18. A method according to claim 16, wherein the mammal is a human.